United States Patent [19]
Lassila

[11] Patent Number: 5,847,220
[45] Date of Patent: Dec. 8, 1998

[54] PROCESS FOR HYDROGENATION OF CYANOPROPIONALDEHYDE-CONTAINING CYANOPROPIONALDEHYDE ACETALS

[75] Inventor: Kevin Rodney Lassila, Macungie, Pa.

[73] Assignee: Air Products and Chemicals, Inc., Allentown, Pa.

[21] Appl. No.: 876,892

[22] Filed: Jun. 16, 1997

[51] Int. Cl.⁶ .................................................. C07C 209/46
[52] U.S. Cl. ............................................................ 564/493
[58] Field of Search ............................................. 564/493

[56] References Cited

U.S. PATENT DOCUMENTS

| | | | |
|---|---|---|---|
| 2,449,036 | 9/1948 | Grunfeld | 260/583 |
| 3,427,356 | 2/1969 | Baer et al. | 260/583 |
| 3,896,173 | 7/1975 | Drake | 260/583 P |
| 4,375,003 | 2/1983 | Allain et al. | 564/492 |

FOREIGN PATENT DOCUMENTS 0316761  11/1988  European Pat. Off. .

*Primary Examiner*—Brian M. Burn
*Attorney, Agent, or Firm*—Russell L. Brewer

[57] ABSTRACT

Disclosed is an improved process for the catalytic hydrogenation of cyanopropionaldehyde alkyl acetals (CPAA) to form the aminobutyraldehyde alkyl acetals. The basic process comprises hydrogenating the cyanopropionaldehyde alkyl acetals by contacting said cyanopropionaldehyde alkyl acetals with hydrogen in the presence of a nickel or cobalt catalyst under conditions for reducing the nitrile group to the primary amine. The improvement resides in effecting the hydrogenation of a cyanopropionitrile dialkyl acetal feedstock containing contaminating levels of cyanopropionaldehyde in the presence of ammonia or a primary amine and alkali metal hydroxide.

9 Claims, No Drawings

PROCESS FOR HYDROGENATION OF CYANOPROPIONALDEHYDE-CONTAINING CYANOPROPIONALDEHYDE ACETALS

BACKGROUND OF THE INVENTION

Aminobutyraldehyde dimethyl acetal (ABAA) is an amine which can be incorporated into polymers to provide crosslinkable functionality useful in coatings formulations. The advantage of coatings technology based on ABAA and other aminoalkylaldehyde alkyl acetals is that it can avoid the use of formaldehyde-based crosslinkers. Legislation requiring reduction of such formaldehyde emissions has become increasingly stringent and coatings formulators and resin manufacturers have become receptive to alternative, more environmentally benign technologies.

ABAA, and other aminopropionaldehyde acetals are typically produced by hydrogenation of the corresponding nitrile, a material in turn produced by catalytic hydroformylation of acrylonitrile in an alcohol solvent. The initially-formed cyanopropionaldehyde is converted under the reaction conditions to the cyanopropionaldehyde acetal by reaction with an alcohol. The reaction product is distilled to remove impurities and then hydrogenated.

The following patents are relevant to the hydrogenation of nitriles:

U.S. Pat. No. 2,449,036 discloses the manufacture of primary amines by the catalytic liquid phase hydrogenation of the corresponding nitrites. In an effort to avoid the formation of secondary and tertiary amines, the hydrogenation was carried out in the presence of ammonia or in the presence of substances capable of liberating ammonia. It should be noted that the addition of ammonia decreases the partial pressure of hydrogen in the reactor and leads to lower rates than in reactions performed in the absence of ammonia. Cobalt catalysts in combination with an alkali metal hydroxide, e.g., sodium, potassium or lithium hydroxide, or quaternary ammonium bases have been found to result in high yields of a primary amine without the concomitant problems associated with the use of ammonia.

U.S. Pat. No. 3,427,356 discloses the preparation of 1,3-propylenediamines by hydrogenating β-aminopropionitriles in the presence of ammonia at temperatures below 200° C., the catalyst for such hydrogenation being cobalt or nickel. The patentees point out that a small amount of a manganese compound dissolved in the hydrogenation mixture enhances the activity of the catalyst with little decomposition of the catalyst or deposition of the polymers thereon.

U.S. Pat. No. 3,896,173 discloses a two stage catalytic hydrogenation of unsaturated dinitriles using ruthenium or nickel as the catalyst. In the process, ammonia is used in the first stage catalytic hydrogenation wherein the nitrile is reduced to the amine. This hydrogenation is followed by a second stage hydrogenation where the ethylenic unsaturation is hydrogenated. Conventional hydrogenation catalysts are deemed suitable for the two staged hydrogenation and these include ruthenium, Raney nickel, and the like.

U.S. Pat. No. 4,375,003 discloses an improved process for preparing primary amines from an aliphatic nitrile and hydrogen. Raney cobalt is used as the catalyst. To avoid the use of ammonia and other bases in an effort to produce primary amines in high yield, a small amount of alkali metal hydroxide and/or ammonia may be added. The catalyst employed is a Raney cobalt catalyst incorporating from 2–35 weight percent aluminum with a cobalt aluminum alloy being contacted with an aqueous medium containing dissolved alkali metal hydroxide.

European 0 316 761 discloses a process for producing N,N-dimethyldiaminopropane by the catalytic hydrogenation of N,N-dimethylaminopropionitrile in the presence of ammonia and one or more alkaline earth oxides. Raney cobalt is the preferred catalyst.

BRIEF SUMMARY OF THE INVENTION

The present invention pertains to an improved process for the catalytic hydrogenation of cyanopropionaldehyde alkyl acetals (CPAA) to form the aminobutyraldehyde alkyl acetals. The basic process comprises hydrogenating the cyanopropionaldehyde alkyl acetals by contacting said cyanopropionaldehyde alkyl acetals with hydrogen in the presence of a nickel or cobalt catalyst under conditions for reducing the nitrile group to the primary amine. The improvement resides in effecting the hydrogenation of a cyanopropionitrile dialkyl acetal feedstock containing contaminating levels of cyanopropionaldehyde in the presence of ammonia or a primary amine and alkali metal hydroxide.

The presence of ammonia or an amine is effective for imparting the following advantages to the hydrogenation process:

it has an ability to overcome the difficulties associated with producing a highly purified cyanoalkylaldehyde alkyl acetal feedstock prior to hydrogenation;

it has an ability to employ a feedstock containing reaction contaminants; and it has an ability to produce the desired primary amine products in high yield and selectivity.

DETAILED DESCRIPTION OF THE INVENTION

This process is useful for the hydrogenation of cyanoalkylaldehyde acetal feeds and particularly cyanopropionitrile dialkyl acetal which contains cyanopropionaldehyde. The reaction chemistry is as follows:

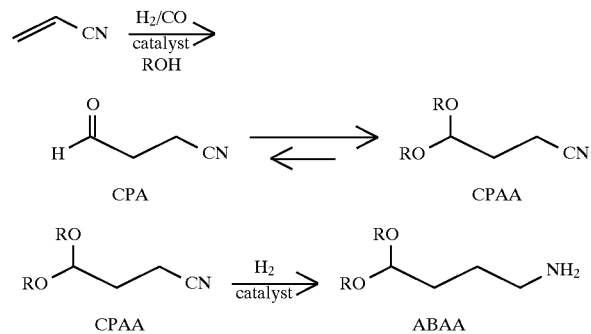

In the above reaction, R is aliphatic, typically alkyl and more particularly an alkyl radical having from 1–8 carbon atoms and alkoxy having from 1–8 carbon atoms. It can also be cycloalkyl or aryl and R may be the same or different. Also, the R group may be the residue of a polyfunctional alcohol which couples to another cyanopropionaldehyde. A representative example is as follows:

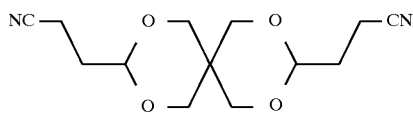

The acetal is formed by reacting the cyanopropionaldehyde with an alcohol. This reaction typically is done in situ although the reaction may be carried out subsequent to the aldehyde formation. Classes of alcohols are $C_{1-8}$ alkanols, $C_{1-8}$ alkoxyalkanols, $C_{2-8}$ glycols and polyols, and aryl alcohols. Examples of alcohols include methanol, ethanol, 1-propanol, 2-propanol, 1-butanol, 2-butanol, and 2-methyl-2-propanol and so on, ethylene glycol, 1,2-propane diol, 1,3-propane diol, 2-methyl-1,3-propanediol, butylene glycol, methoxypropanol, ethoxyethanol, cyclohexanol, sorbitol, glycerol, pentaerythritol phenol and benzyl alcohol. Acetals derived from hydroxyl-containing polymers such as polyvinyl alcohol, polyether polyols, and polyester polyols as also applicable for the formation of the acetal. The condensation product derived by the reaction of cyanopropionaldehyde with tetrols can also be employed.

The acetal formation is an equilibrium-controlled process. In the past it has been necessary to rigorously purify the reaction product to remove impurities otherwise hydrogenation was ineffective. It has been found that the presence of only a few tenths of a percent or so of cyanopropionaldehyde in the reaction product can completely inhibit the hydrogenation of the cyanopropionaldehyde alkyl acetals, and even trace quantities can result in an extensive induction period. Because rigorous fractional distillation had been required this process step diminished the efficiency and adversely effected the economics of cyanopropionitrile dialkyl acetal production.

To overcome the problems associated with rigorous distillation it has been found that the hydrogenation of relatively crude streams of cyanopropionaldehyde alkylacetals can be effected in the presence of amines. Amines which can be used for this hydrogenation reaction include ammonia and aliphatic primary amines. In addition to conventional alkyl mono amines, this group includes: alkylene diamines, triamines, and so on; cycloaliphatic amines such as cyclohexyl amine and bis(-p-aminocyclohexyl) amine (PACM); polymeric primary amine-containing materials such as homo- and copolymers of polyvinyl amines. Examples include $C_{1-8}$ alkyl amines such as methyl, ethyl, propyl, butyl amine, $C_{2-8}$, ethylene amine streams such as ethylene diamine, diethylene triamine, triethylene tetramine, aminoethylpiperazine, cyclohexylamine, and the like.

The amount of amine added must be sufficient to substantially consume the aldehyde present in the reaction mixture. That is, at least approximately one molar equivalent of amine based on aldehyde is consumed. Somewhat less may be possible in certain cases, but much less than one equivalent per aldehyde equivalent is unlikely to allow the facile hydrogenation that is required. Substantially, more than one amine equivalent aldehyde can be added without ill effect, except that in extreme cases, reactor productivity may suffer. Typically, from 1.1 to 1.5 equivalents amine per equivalent aldehyde is employed.

Alkali metal hydroxide is incorporated into the hydrogenation medium in an amount from about 0.1 to 1% to based upon the weight of the cyanoalkylaldehyde alkyl acetal feedstock. Too little alkali metal hydroxide can adversely affect the selectivity to the desired aminobutyraldehyde dialkylacetal and lead to larger amounts of secondary amine byproducts. Too much alkali metal hydroxide can diminish the activity of the catalyst and lead to long reaction times. Alkali metal hydroxides include sodium, potassium and lithium hydroxide.

The catalysts employed in the reaction include the conventional nickel and cobalt hydrogenation catalysts. Examples include Raney nickel and Raney cobalt. Also, supported nickel and cobalt catalysts may be employed, the supports generally comprising alumina. Other components such as promoters may be incorporated into the catalyst, e.g., manganese.

The reaction should be run at a temperature sufficient to provide a convenient reaction rate, but low enough to prevent thermal decomposition of the reagents, products, or catalyst. Temperatures from about 40° C. to about 150° C. may be employed, with temperatures from 60° to 120° C. being preferred. Below these temperatures, the rate of reaction is inconveniently low, whereas above these temperatures, decomposition of the product begins to occur.

The reaction should be run at a pressure sufficient to induce reaction. Pressures from about 100 psig to about 5000 psig are suitable, preferably about 100–800 psig. Pressures much lower than 100 psig would probably provide an inconveniently low reaction rate. Pressures above 5000 psig would work, but it is not anticipated that these high pressures would provide significant advantage and in all likelihood increase the cost of the capital required to practice the invention.

The process may be practiced in the presence of inert solvents such as alcohols, ethers, esters, amines, and so on. Practicing in the presence of a solvent may provide processing or other benefits, but that may decrease reactor productivity.

The following examples are provided to illustrate various embodiments of the invention and comparisons thereto and are not intended to restrict the scope thereof.

Comparative Example 1

Hydrogenation of Cyanopropionaldehyde Dimethyl Acetal Free of Cyanopropionaldehyde Using Nickel Catalyst A 1 L autoclave was charged with A4000 chrome-promoted sponge nickel catalyst (marketed by Activated Metals and Chemicals, 4.8 g) in 5 g of water, and cyanopropionaldehyde dimethyl acetal, 625 g. GC analysis of the cyanopropionaldehyde dimethyl acetal showed that it was free of cyanopropionaldehyde. A solution of $LiOH.H_2O$ (2.1 g) in $H_2O$ (10 mL) was added. Then, the reactor was sealed, purged free of air and the pressure checked with nitrogen. Hydrogen was introduced and the hydrogen pressure adjusted to ca. 500 psig; the reaction mixture was heated to 90° C. When the temperature had equilibrated, the pressure was increased to 750 psig, and maintained by means of a regulated ballast. After about 14 h, the theoretical amount of hydrogen had been consumed and the hydrogen uptake was complete. The product was removed from the reaction vessel and analyzed by GC. Aminobutyraldehyde dimethyl acetal had been formed in 92% yield (molar basis).

Comparative Example 2

Hydrogenation of Cyanopropionaldehyde Dimethyl Acetal in the Presence of Cyanopropionaldehyde Using Nickel Catalyst A cyanopropionaldehyde dimethyl acetal feed was analyzed by GC and found to contain 1.9% cyanopropionaldehyde. Hydrogenation of this material was attempted using the procedure of Comparative Example 1. After 16 h at 90° C. and 750 psig, less than 2% of the theoretical quantity of hydrogen had been consumed. GC analysis of the dark brown product showed that it contained only 1.7% aminobutyraldehyde dimethyl acetal, and 94.9% of the material was comprised of unreacted cyanopropionaldehyde dimethyl acetal.

These results show the severe and adverse impact of the presence of contaminant cyanopropionaldehyde on the hydrogenation of cyanopropionaldehyde dimethyl acetal. In Example 1, the yield was approximately 92% while in this example there was essentially no reaction and almost all of the starting cyanopropionitrile dialkyl acetal remained unconverted.

Example 3

Hydrogenation of Cyanopropionaldehyde Dimethyl Acetal in the Presence of Cyanopropionaldehyde and Ammonia Using Nickel Catalyst A 1 L autoclave was charged with A4000 nickel catalyst and the cyanopropionaldehyde dimethyl acetal feed as described in Comparative Example 2. The reactor was sealed, then purged free of air and pressure checked with nitrogen followed by addition of hydrogen. The reactor was vented to atmospheric pressure and then anhydrous ammonia (38 g) was added. The hydrogenation was performed at 90° C. and ca. 750 psig. After 15 h, hydrogen uptake was complete, and the product was removed from the reactor. GC analysis showed that the reaction product was comprised of 2.6% unreacted cyanopropionaldehyde dimethyl acetal, 82.8% aminobutyraldehyde dimethyl acetal, 7.4% bis-(4,4,-dimethoxybutyl)amine, and 6.1% unidentified materials.

The fact that addition of ammonia increases the action rate for hydrogenation of a nitrile was quite unexpected. Addition of ammonia to the reaction decreases the partial pressure of hydrogen and thus would be expected to diminish the rate of reaction and, hence, reduce the observed conversion.

Example 4

Hydrogenation of Cyanopropionaldehyde Dimethyl Acetal in the Presence of Cyanopropionaldehyde and n-Butyl Amine Using Nickel Catalyst A cyanopropionaldehyde dimethyl acetal feed was analyzed and found to contain 5.1% cyanopropionaldehyde. A 1 L autoclave was charged with A4000 sponge nickel catalyst (4.67 g in 13.7 g $H_2O$). n-Butyl amine (42.0 g) was added to the cyanopropionaldehyde dimethyl acetal feed and the combined materials added to the reactor. A solution of $LiOH.H_2O$ (2.5 g) in $H_2O$ (11 mL) was added. The reactor was sealed, then purged free of air and pressure checked with nitrogen followed by hydrogen. The hydrogen pressure was adjusted to ca. 200 psig and the reaction mixture was heated to 90° C. When the temperature had equilibrated, the pressure was increased to 750 psig, and maintained there by means of a regulated ballast. After about 14 h, the theoretical amount of hydrogen had been consumed and hydrogen uptake was complete. The product was removed from the reaction vessel and analyzed by GC. GC analysis showed the reaction mixture contained 0.1% unreacted cyanopropionaldehyde dimethyl acetal, 80.2% aminobutyraldehyde dimethyl acetal, 4.2% secondary amine, and 15.7% other products. Based upon contained cyanopropionaldehyde dimethyl acetal, the conversion was 99.9% and the selectivity to aminobutyraldehyde dimethyl acetal was 94.5%. These results show that n-butyl amine is effective in countering the poisoning effects of cyanopropionaldehyde in the hydrogenation process.

Example 5

Hydrogenation of Cyanopropionaldehyde Dimethyl Acetal in the Presence of Cyanopropionaldehyde and 3-Dimethylaminopropyl Amine Using Nickel Catalyst The cyanopropionaldehyde dimethyl acetal feed and procedure of Example 4 were used except that 3-dimethylaminopropyl amine (DMAPA) (68.1 g), rather than n-butyl amine, was added to the cyanopropionaldehyde dimethyl acetal feed. The temperature of the cyanopropionaldehyde dimethyl acetal feed rose 11° C. after the addition. The hydrogenation was complete in 8 h. GC analysis of the reaction product showed that it contained unreacted cyanopropionaldehyde dimethyl acetal (1.4%), aminobutyraldehyde dimethyl acetal(73.4%), bis-(4,4-dimethoxybutyl)amine (7.4%) and other products (17.8%). The conversion of cyanopropionaldehyde dimethyl acetal was 98.2% and the selectivity to aminobutyraldehyde dimethyl acetal was 91.7%.

This example illustrates that the hydrogenation can be carried out in the presence of 3-dimethylaminopropyl amine (DMAPA) without the effects associated with cyanopropionaldehyde.

Comparative Example 6

Hydrogenation of Cyanopropionaldehyde Dimethyl Acetal in the Presence of Cyanopropionaldehyde and Di-n-butylamine Using Nickel Catalyst The feed and procedure of Example 4 was used except that di-n-butylamine (74.5 g), rather than n-butyl amine, was added to the feed. The temperature of the cyanopropionaldehyde dimethyl acetal feed rose 3° C. after the addition. After 16 h at 90° C. and ca. 750 psig, only about 6% of the theoretical quantity of hydrogen had been consumed. GC analysis of the reaction product indicated that the composition was unreacted cyanopropionaldehyde dimethyl acetal (78.9%), aminobutyraldehyde dimethyl acetal, (0.2%), di-n-butyl amine (17.9%), and other materials (3.2%).

This example illustrates that secondary amines, such as di-n-butylamine, are ineffective in the hydrogenation process for overcoming the poisoning due to the presence of cyanopropionaldehyde.

Comparative Example 7

Hydrogenation of Cyanopropionaldehyde Dimethyl Acetal in the Presence of Cyanopropionaldehyde and Aniline Using Nickel Catalyst The feed and procedure of Example 4 was used except that aniline (53.6 g), rather than n-butyl amine, was added to the cyanopropionitrile dialkyl acetal feed. The temperature of the cyanopropionaldehyde dimethyl acetal feed rose 7° C. after the addition. After attempted hydrogenation for 19 h at 90° C. and ca. 750 psig $H_2$, only about 5% of the theoretical quantity of hydrogen had been consumed. GC analysis of the reaction product indicated that the composition was unreacted cyanopropionaldehyde dimethyl acetal (81.4%), aminobutyraldehyde dimethyl acetal (0.3%), aniline (14.3%), and other materials (0.8%).

This example shows that aromatic amines, such as aniline, are ineffective in the hydrogenation process for overcoming the poisoning due to the presence of cyanopropionaldehyde.

Example 8

Hydrogenation of Cyanopropionaldehyde Dimethyl Acetal in the Presence of Cyanopropionaldehyde and ABAA Using Nickel Catalyst A 2500 gallon reactor containing the catalyst and about 1200 lb. of the crude ABAA product from a reaction was charged with 13,248 lb. of cyanopropionaldehyde dimethyl acetal containing 0.14 wt % cyanopropionaldehyde. A solution of 22 lb. of LiOH hydrate in 25 gallons of water was added and the reaction was initiated. Hydrogen uptake began immediately; no induction period was observed. After 19 h at 80° C. and ca. 700 psig, H$_2$ uptake was complete. Aminobutyraldehyde dimethyl acetal was formed in 91% yield.

This example illustrates that the aminobutyraldehyde dimethyl acetal product of the reaction, itself, can be used to overcome the catalyst poisoning associated with cyanopropionaldehyde provided it is present in the reaction medium prior to hydrogenation.

Comparative Example 9

Hydrogenation of Cyanopropionaldehyde Diethyl Acetal in the Presence of Cyanopropionaldehyde Using Cobalt Catalyst Cyanopropionaldehyde diethyl acetal (350 g) containing 0.2 wt % cyanopropion-aldehyde was loaded into a 1 liter autoclave reactor. Raney Cobalt (marketed under the designation 2724 by W. R. Grace) 5.7 g was added. The reactor was purged with several nitrogen pressure vent cycles followed by three pressure vent cycles with hydrogen. The reactor was then pressured to 500 psig with H$_2$ and heated to 100° C. When the reactor reached 100° C. the hydrogen pressure was increased to 850 psig. After 10 hrs at 100° C. and 850 psig only 4% of the theoretical hydrogen had been consumed. This example illustrates that the limitations of Comparative Example 2 apply to attempted hydrogenations of not only the dimethyl acetal but also the diethyl acetal of cyanopropionaldehyde and that the limitations apply to cobalt catalysts as well as nickel.

Example 10

Hydrogenation of Cyanopropionaldehyde Diethyl Acetal in the Presence of Cyanopropionaldehyde and Dimethylaminopropyl Amine Using Cobalt Catalyst This experiment was carried out in a 300 mL autoclave reactor in similar manner to Example 9. However, the ratio of catalyst to cyanopropionaldehyde diethyl acetal was kept constant in order to provide a comparison with other experiments. To the 300 mL reactor was added cyanopropionaldehyde diethyl acetal (80 g containing about 0.2% cyanopropionaldehyde, same as Example 2), Raney Co 2724 (1.35 g) and dimethylaminopropyl amine (DMAPA, 2.8 g). The reactor was purged with several nitrogen pressure vent cycles followed by three pressure vent cycles with hydrogen. The reactor was then pressured to 500 psig with H$_2$ and heated to 100° C. When the reactor contents reached 100° C., the reactor was pressured to 850 psig. Hydrogen uptake ceased in 8 hrs. Product analysis by internal standard gas chromatography showed 100% conversion of cyanopropionaldehyde diethyl acetal with 93.9% selectivity to aminobutyraldehyde diethyl acetal.

These results show that hydrogenation of cyanopropionaldehyde-containing cyanopropionaldehyde diethyl acetal using a Raney cobalt catalyst can be effected in the presence of DMAPA.

What is claimed is:

1. In a process for the catalytic hydrogenation of a cyanopropionaldehyde alkyl acetal by contacting said cyanopropionaldehyde alkyl acetal with hydrogen in the presence of a nickel or cobalt catalyst under conditions for reducing the nitrile group to the primary amine, the improvement which resides in effecting the hydrogenation of said cyanopropionaldehyde alkyl acetal containing contaminating levels of cyanopropionaldehyde in the presence of ammonia or a primary amine and alkali metal hydroxide.

2. The process of claim 1 wherein the cyanopropionaldehyde alkyl acetal is represented by the formula:

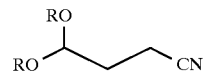

wherein R is the residue of an aliphatic or aryl alcohol and R may be the same or different.

3. The process of claim 2 wherein R in said formula is an alkyl radical having from 1–8 carbon atoms or alkoxy having from 1–8 carbon atoms.

4. The process of claim 3 wherein the primary amine incorporated in the hydrogenation process is selected from the group consisting of C$_{1-8}$ alkyl amines, C$_{2-8}$ polyethylene amines, aminoethylpiperazine, aminobutyraldehyde dialkyl acetal and cyclohexylamine.

5. The process of claim 4 wherein the catalyst is selected from the group consisting of Raney cobalt and Raney nickel.

6. The process of claim 5 wherein the primary amine incorporated in the incorporated in the amount of from about 1.1 to 1.5 equivalents amine per equivalent aldehyde.

7. The process of claim 3 wherein the R designating the alcohol residue is the residue from an alcohol selected from the group consisting of C$_{1-8}$ alkanols, C$_{1-8}$ alkoxyalkanols, C$_{2-8}$ glycols and polyols, and aryl alcohols.

8. The process of claim 7 wherein the primary amine incorporated in the reaction is selected from the group consisting of methyl amine, ethyl amine, propyl amine, butyl amine and aminobutyraldehyde diethyl acetal.

9. The process of claim 3 wherein the cyanopropionaldehyde alkyl acetal is prepared with methanol or ethanol.

* * * * *